US00PP08362P

United States Patent [19]

McGredy, IV

[11] Patent Number: Plant 8,362

[45] Date of Patent: Sep. 7, 1993

[54] FLORIBUNDA ROSE PLANT NAMED MACIVY

[75] Inventor: Sam McGredy, IV, Auckland, New Zealand

[73] Assignee: Roses by Fred Edmunds, Inc., Wilsonville, Oreg.

[21] Appl. No.: 833,844

[22] Filed: Feb. 5, 1992

[51] Int. Cl.[5] ..... A01H 5/00

[52] U.S. Cl. ..... Plt./22

[58] Field of Search ..... Plt./22, 25, 26, 27

*Primary Examiner*—Howard J. Locker

*Attorney, Agent, or Firm*—Christie, Parker & Hale

[57] ABSTRACT

A new variety of floribunda rose having multi-colored apricot and red flowers.

2 Drawing Sheets

SUMMARY OF THE INVENTION

The present invention relates to a new and distinct variety of rose plant of the floribunda rose class, which was originated by my crossing as seed parent the variety known as 'Sexy Rexy' (U.S. Plant Pat. No. 6,713) and as pollen parent the variety known as 'Pot of Gold'. The varietal denomination of this new rose is 'Macivy'.

Among the novel characteristics possessed by this new variety which distinguishes it from its parents and all other varieties of which I am aware are its attractive multi-colored flowers of apricot tones and red tones which convey an impression of copper-apricot shades of color borne in clusters on a plant suitable for growing outdoor in gardens.

Asexual reproduction by propagation by budding of the new variety as performed in Wilsonville, Oreg. shows that the foregoing and other distinguishing characteristics come true to form and are established and transmitted through succeeding propagations.

BRIEF DESCRIPTION OF ILLUSTRATION

The accompanying illustrations show typical specimens of the vegetative growth and flowers of the new variety in different stages of development depicted in color as nearly true as it is reasonably possible to make the same in a color illustration of this character.

DETAILED DESCRIPTION OF THE NEW VARIETY

The following is a detailed description of my new variety, with color terminology in accordance with The Royal Horticultural Society Colour Chart (R.H.S.C.C.). The terminology used in the color descriptions herein refers to plate numbers in the aforementioned color chart.

Parentage: Seedling.

*Seed parent.*—'Sexy Rexy'.

*Pollen parent.*—'Pot of Gold'.

Class: Floribunda.

The following further horticultural observations wre made of specimens grown outdoor in Wilsonville, Oreg. in the month of October.

FLOWER

Blooming habit: Continuous.

A. Bud:

(1) *Size.*—Medium, about 3 cm. long.

(2) *Form.*—Urn shaped.

(3) *Color.*—As sepals divide, near 41A to 42A.

(4) *Sepals.*—Simple, longer than bud — wooly inside, glabrous outside with scattered glandular hairs — color near to 144B, outside nearly white inside because of wooly hairs.

(5) *Peduncle.*—Length — short, about 3–4 cm. Aspect — straight. Strength — erect. Color — near to 144C (smooth — no prickles present).

(6) *Bracts.*—Usually 2 to 4, leaflet-like, at upper stem, near to 137A (top).

Bloom:

(1) *Size.*—Medium, about 7–8 cm.

(2) *Borne.*—Sprays, generally three to fifteen blooms — terminal bloom on larger sprays opens and blows prematurely. The side buds with leafy bracts open almost simultaneously a day later.

(3) *Form.*—Urn shaped at first flexing outwardly in a spiral, becoming ruffled at maturity, petaloids usually cover stamens.

(4) *Petalage.*—Number of petals under normal conditions — about 30 to 35.

(5) *Color.*—Upon separation of sepals, color of bud is near 42A to 41A with yellow near base. As petals unfurl and flowers open, multi coloration is evident. Petal top surface tends to near mixed shades of near 27A to B at inner petals to near 55D and lighter at middle petals with deeper tones, near 55C at outer petals concluding with near 55B to C at some petal edges and apices washing into petal margins. Interesting tan coloration near 165D to 168D appears where petals bunch and at centers of fully open blooms. Petal undersurface, first visible in buds, exhibits darker coloration, near 48A to 50B to 51A to B, lightening to apricot pink tonality similar to petal top surface on inner petals, especially in fully open blooms. Yellow coloration, near 21A to B, is distinct near point of petal attachment in petal undersurface from bud to opening blooms. As flowers age, overall coloration tends to lighten.

C. Petals:

(1) *Texture.*—Thick.

(2) *Appearance.*—Inside smooth and outside satiny with slight veining apparent on the outside only.

(3) *Form.*—Deltoid.

(4) *Arrangement.*—Imbricated, spiralled to a point.

(5) *Petaloids in center.*—Few, incurved.
(6) *Persistence.*—Drop off cleanly.
(7) *Fragrance.*—Sweet, musky.
(8) *Lasting Quality.*—On plant — approximately 10 to 14 days. Cut flower — approximately 5 to 7 days.

REPRODUCTIVE ORGANS

A. Stamens, filaments and anthers:
*Arrangement.*—Regularly arranged around styles, irregular length.
*Color.*—Near to 15A.
B. Pollen:
*Color.*—Near to 23B.
C. Styles: Tightly bunched and contorted.
*Color.*—Near to 39B.
D. Stigmas: Spongy, near to 4C.
E. Hips: None observed.

PLANT

A. Form: Upright, compact.
B. Growth: Free branching.
*Height attained.*—About 100 to 120 cm.
C. Foliage: Compound usually 5 leaflets — many 3 leaf bracts in inflorescence.
(1) *Size.*—Small.
(2) *Quality.*—Abundant, close set.
(3) *Color.*—New foliage: Upper side — near to 59A. Under side — near to 59A. Old foliage: Upper side — near to 139A. Under side — near to 137C.
(4) *Shape.*—Ovoid, acuminate.

(5) *Texture.*—Upper side is leathery, lustrous, veins barely evident; under side is flat; mid rib veins — barely prominent.
(6) *Edge.*—Serrate.
(7) *Serration.*—Simple.
(8) *Petiole color.*—Top surface — near 144C. Undersurface — near 144B.
(9) *Stipules.*—Long — extending ½ to ⅔ the distance to the first leaflets, slightly bearded.
(10) *Auricle.*—Narrow.
(11) *Rachis.*—Smooth, slightly cupped.
(12) *Resistance to disease.*—Blackspot — Excellent. Mildew — Excellent. Rust — Excellent.
D. Wood:
(1) *New wood.*—Color — near to 144A. Bark — smooth, shiny.
(2) *Old wood.*—Color — near to 146A. Bark — smooth.
E. Thorns:
*Quantity (main stalk).*—Few.
*On laterals from stalk.*—Few to none.
*Form.*—Broad base, slightly recurved.
*Length.*—Medium.
*Color.*—Near to 144C (when young).
*Position.*—Irregular.
*Prickles.*—None.
F. Winter hardiness: Winter hardy but needs protection in severe climates.

I claim:

1. A new and distinct variety of rose plant of the floribunda rose class, substantially as shown and described.

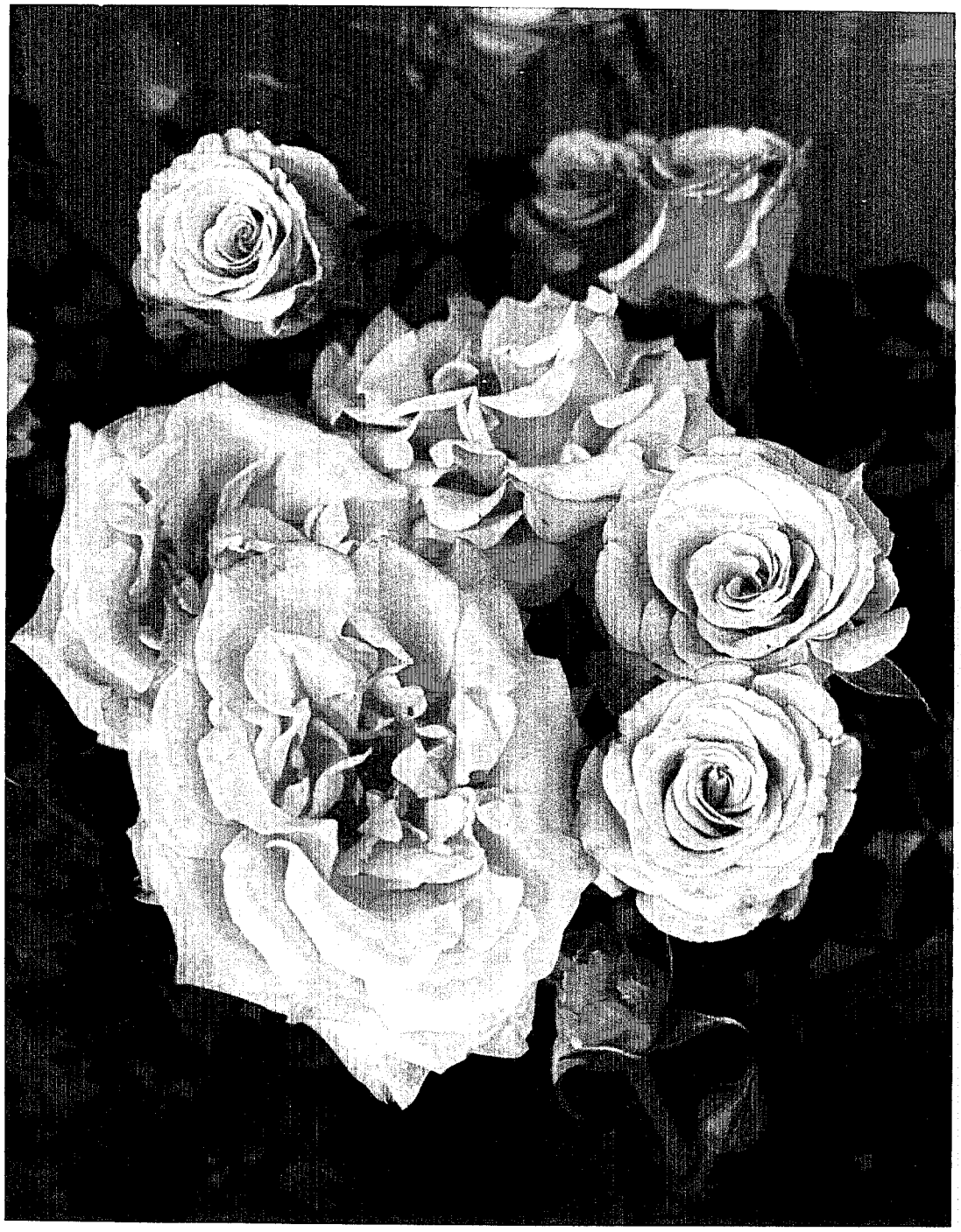

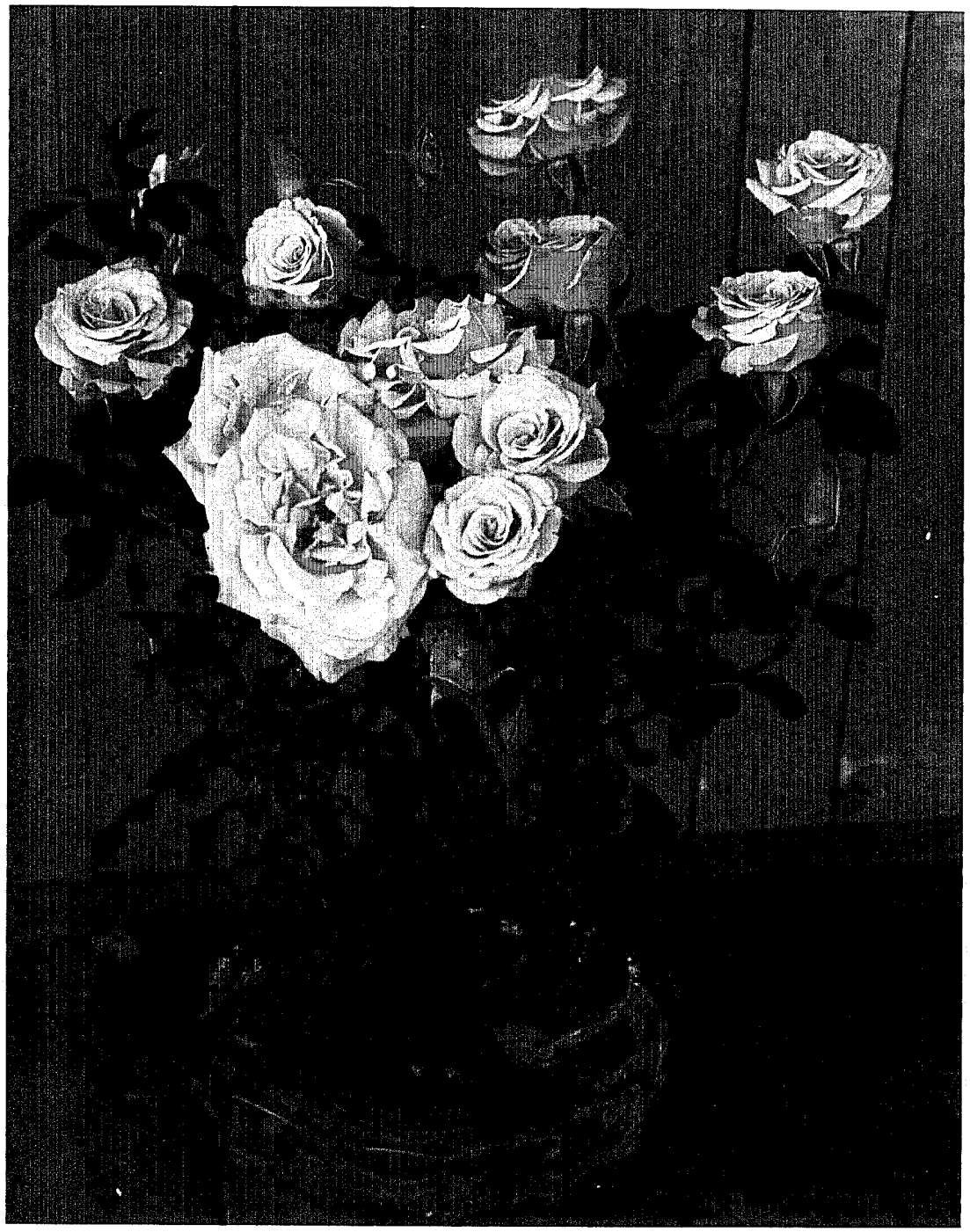

* * * * *